United States Patent [19]

Gubin et al.

[11] 4,103,012
[45] Jul. 25, 1978

[54] INDOLIZINE DERIVATIVES, PHARMACEUTICAL COMPOSITIONS AND METHODS CONTAINING SAME

[75] Inventors: Jean Gubin, Brussels; Gilbert Rosseels, Meise, both of Belgium

[73] Assignee: Labaz, Paris, France

[21] Appl. No.: 769,332

[22] Filed: Feb. 16, 1977

[30] Foreign Application Priority Data

Feb. 19, 1976 [GB] United Kingdom ............... 06680/76
Aug. 10, 1976 [GB] United Kingdom ............... 33314/76

[51] Int. Cl.² .................... A61K 31/44; C07D 221/22
[52] U.S. Cl. ............................... 424/263; 260/293.61; 260/294.8 R; 544/362; 544/127
[58] Field of Search ........ 260/297 B, 296 B, 294.8 R; 424/263

[56] References Cited

PUBLICATIONS

Dainis, Chem. Abstracts, vol. 77, (3), 19,499f, Jul. 17, 1972.
Dainis, Chem. Abstracts, vol. 77, (5), 34,269z, Jul. 31, 1972.
Dainis, Chem. Abstracts, vol. 77, (13), 88,260h, Sep. 25, 1972.
Rosseels et al., Chem. Abstracts, vol. 84, (21), 150,535b, May 24, 1976.

*Primary Examiner*—Alan L. Rotman
*Attorney, Agent, or Firm*—Mason, Kolehmainen, Rathburn & Wyss

[57] ABSTRACT

Novel indolizine derivatives of the general formula:

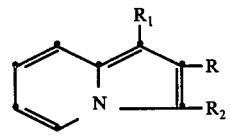

and pharmaceutically acceptable acid addition salts thereof, wherein R represents a branched- or straight-chain alkyl radical having from 1 to 5 carbon atoms, a phenyl radical, a mono-fluoro-, mono-chloro- or mono-bromo-phenyl, a di-fluoro-, di-chloro- or di-bromo-phenyl radical, a methoxy-phenyl radical or a methyl-phenyl radical optionally substituted on the aromatic moiety by an atom of fluorine, chlorine or bromine and $R_1$ and $R_2$, which are different, represent a hydrogen atom or a group of the formula:

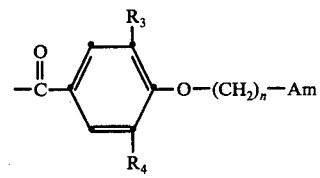

wherein $R_3$ and $R_4$, which are identical, each represent a hydrogen atom or a methyl radical, Am represents a dimethylamino, diethylamino, di-n-propylamino, di-n-butylamino, morpholino, piperidino, pyrrolidino or 4-methyl-piperazino group and n is an integer in the range of from 2 to 6 inclusive.

They are effective for treating certain pathological or otherwise abnormal conditions of the heart and more particularly sinus tachycardia. Certain of them are also useful in the treatment of angina pectoris and cardiac arrhythmia.

16 Claims, No Drawings

INDOLIZINE DERIVATIVES, PHARMACEUTICAL COMPOSITIONS AND METHODS CONTAINING SAME

This invention relates to heterocyclic compounds and is concerned with novel indolizine derivatives and with a method for preparing the said novel derivatives.

The indolizine derivatives with which the present invention is concerned are the compounds represented by the general formula:

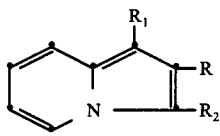   I and the pharmaceutically acceptable acid addition salts thereof, for example the oxalate, hydrochloride or methanesulphonate, wherein R represents a branched- or straight-chain alkyl radical having from 1 to 5 carbon atoms, a phenyl radical, a mono-fluoro-, mono-chloro- or mono-bromo-phenyl, a di-fluoro, di-chloro- or di-bromo-phenyl radical, a methoxy-phenyl radical or a methyl-phenyl radical optionally substituted on the aromatic moiety by an atom of flourine, chlorine or bromine and $R_1$ and $R_2$, which are different, represent a hydrogen atom or a group of the formula:

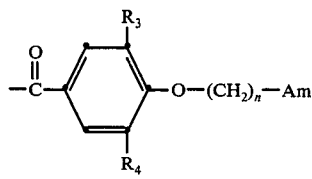

wherein $R_3$ and $R_4$, which are identical, each represent a hydrogen atom or a methyl radical, Am represents a dimethylamino, diethylamino, di-n-propylamino, di-n-butylamino, morpholino, piperidino, pyrrolidino or 4-methyl-piperazino group and $n$ is an integer in the range of from 2 to 6 inclusive.

The present invention is also concerned with pharmaceutical or veterinary compositions containing, as active principle at least one indolizine derivative of formula I or a pharmaceutically acceptable acid addition salt thereof, in association with a pharmaceutical carrier or excipient therefor.

Another object of the present invention is to provide a process for preparing pharmaceutical or veterinary compositions whereby at least one indolizine derivative of formula I or a pharmaceutically acceptable acid addition salt thereof, is associated with a pharmaceutical carrier or excipient therefor.

The indolizine derivatives of the invention have been found to possess useful pharmacological properties capable of rendering them of considerable value in the treatment of certain pathological or otherwise abnormal conditions of the heart, more particularly in cases of sinus tachycardia of various origins.

Compounds within the scope of the invention have also been found to possess properties capable of rendering them extremely useful in the treatment of angina pectoris.

Similarly, compounds of the invention have also been found to be useful for the treatment of cardiac arrhythmia of various origins.

Yet another object of the present invention is to provide a method of treating pathological conditions of the heart and particularly tachycardia, angina pectoris and arrhythmia in a subject in need of such treatment which method comprises administering to said subject an effective dose of at least one indolizine derivative of formula I or a pharmaceutically acceptable acid addition salt thereof.

Daily dosages will be preferably from 100 mg to 300 mg of active principle by oral route and preferably from 2 to 3 mg of active principle by parenteral route to a human being weighing 60 kilos.

The compounds of formula I can be prepared, in accordance with the invention, by condensing, advantageously in an inert medium such as, for example, acetone or methyl ethyl ketone, an alkali metal salt, preferably the potassium or sodium salt, of an appropriately substituted indolizine corresponding to the general formula:

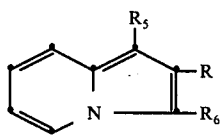   II wherein R has the same meaning as in formula I and $R_5$ and $R_6$, which are different, represent hydrogen or a benzoyl radical of the formula:

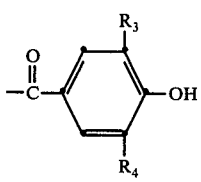

in which $R_3$ and $R_4$ have the same meanings as in formula I, with a dibromoalkane of the general formula:

   III $$Br-(CH_2)_n-Br$$

in which $n$ has the same meanings as in formula I, to form a substituted bromoalkoxy-benzoyl-indolizine of the general formula:

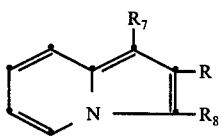   IV wherein R has the same meaning as in formula I and $R_7$ and $R_8$, which are different, represent hydrogen or a benzoyl radical of the general formula:

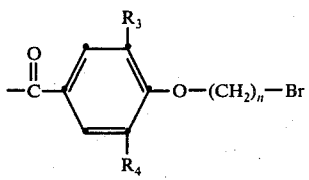

in which $R_3$, $R_4$ and $n$ have the same meanings as in formula I, and condensing the compound of formula IV with a secondary amine of the general formula:

H—Am    V in which Am has the same meaning as in formula I, advantageously in an inert solvent such as, for example, benzene or toluene, to form the required indolizine derivative of formula I which, if desired, is reacted with an appropriate organic or inorganic acid to provide a pharmaceutically acceptable acid addition salt thereof.

The compounds of formula I in which $n$ is 2 or 3 may alternatively be prepared by condensing, advantageously in an aprotic solvent such as, for example, acetone or methyl ethyl ketone, an alkali metal salt, preferably the potassium or sodium salt, of an appropriately substituted indolizine derivative represented by the general formula II with an alkylamino derivative of the general formula:

Z—(CH$_2$)$_n$—Am    VI or an acid addition salt thereof, in which Z represents a halogen atom or a p-toluenesulphonyloxy group and Am has the same meaning as in formula I to give the required indolizine derivative which, if desired, is reacted with an appropriate organic or inorganic acid to provide a pharmaceutically acceptable acid addition salt thereof.

The compounds of formula II can be obtained by hydrolysing in an alkaline medium, the indolizine derivative represented by the general formula:

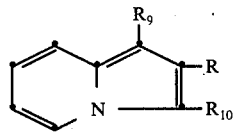

wherein R has the same meaning as in formula I and $R_9$ and $R_{10}$, which are different, represent hydrogen or a 4-tosyloxy radical of the general formula:

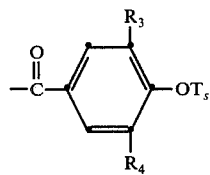

wherein $R_3$ and $R_4$ have the same meanings as in formula I and Ts represents a p-toluenesulphonyl group.

The compounds of formula VII can be obtained by two different processes according to their chemical structure, namely:

(a) When $R_9$ represents a radical of the formula VII A and $R_{10}$ represents hydrogen, by reacting in the presence of aluminium chloride a 3-acetyl-2-R-indolizine, wherein R has the same meaning as in formula I, with a benzoyl chloride derivative of the general formula:

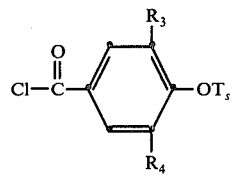

wherein $R_3$, $R_4$ and Ts have the meanings given above, hydrolysing the complex so formed to obtain the corresponding diketone and subsequently removing, in a selective manner, the acetyl group by means of concentrated hydrochloric acid to obtain the required compound of formula VII.

This method has been described by ROSSEELS et al in Eur. J. Med. Chem. 1975, 10, 579.

(b) When $R_9$ represents hydrogen and $R_{10}$ represents a radical of the formula VII A by condensing in an aprotic medium a benzoyl chloride derivative of formula VIII with a 2-R-indolizine wherein R has the same meaning as in formula I in accordance with the method described by D. O. HOLLAND and J. M. C. NAYLER in J. Chem. Soc. 1955, 1504.

The benzoyl chloride derivative of formula VIII wherein $R_3$ and $R_4$ each represent hydrogen is a known compound having been published in J. Amer. Chem. Soc., 78, 2543 (1956). The other compound of formula VIII, namely that in which $R_3$ and $R_4$ each represent methyl can be obtained in accordance with the method described in the aforesaid reference.

The above-mentioned 3-acetyl-2-R-indolizines can be produced by reacting the corresponding 2-R-indolizines with acetic anhydride in the presence of sodium acetate following the method described by E. T. BORROWS et al in J. Chem. Soc. 1946, 1069.

Amongst the above-mentioned 2-R-indolizines, the 2-alkyl derivatives are known compounds having been described either by DAINIS et al in Austr. J. Chem. 1972, 25, 1025 or by ROSSEELS et al in Eur. J. Med. Chem. 1975, 10, 579. They can be prepared from 1-ethoxycarbonylmethyl-2-methyl-pyridinium chloride, the appropriate sodium salt of formula R-COON$_a$ and the anhydride of formula (R—CO)$_2$O wherein R represents an alkyl radical as defined in formula I.

With respect to the 2-aryl-indolizines, some of these compounds are known having been cited by ROSSEELS et al in the aforesaid publication in Eur. J. Med. Chem. The others can be prepared by known procedures. For example, the 2-aryl-indolizines in question can be obtained by first reacting 2-picoline and a 1-R-2-bromo-ethanone and subsequently cyclizing the picolinium derivative so obtained, by means of sodium hydrogenocarbonate.

Heterocyclic compounds having an alkylaminoalkoxybenzoyl chain are already known which are useful in the treatment of pathological conditions of the heart. In this connection, British Pat. Nos. 995,367 and 1,357,212 may be cited which cover dialkylaminoalkoxybenzoyl benzofurans and dialkylaminoalkoxybenzoyl benzothiophenes respectively. The characteristic of such compounds is that they contain a basic heterocyclic nucleus in their molecule, the heteroatom being an oxygen or sulphur atom. It has furthermore been observed that dialkylaminoalkylbenzoyl indoles and pyridines do not present any pharmacological potentialities likely to render them useful in the treatment of cardiac deficiencies. For example, pharmacological tests carried out with more than 75 indole derivatives having the above-mentioned chemical structure were found to be totally inactive as anti-anginal agents.

It would thus appear that the replacement of the benzofuranyl or benzothienyl moiety in dialkylaminoalkoxybenzoyl benzofurans or benzothiophenes by a commonly used nitrogen-containing heterocyclic radical, such as indole or pyridine, is incapable of leading to pharmacological compounds useful in the treatment of angina pectoris.

It has now been found, quite surprisingly, that the replacement of the heterocyclic moiety of dialkylaminoalkoxybenzoyl benzofurans and benzothiophenes by a nitrogen-containing heterocycle, namely indolizine, is capable of providing compounds presenting powerful pharmacological properties useful in the treatment of cardiac deficiencies. This observation is still more unexpected when it is considered that the indolizine moiety is practically unused in the pharmaceutical field. The idea of preparing the indolizine derivatives of the invention as well as their pharmacological activity could not consequently, be in any way deduced from the state of the art.

As mentioned above, the indolizine derivatives of the invention have been found to present pharmacological properties useful in the treatment of sinus tachycardia, angina pectoris and cardiac arrhythmia.

Sinus tachycardia is due to increased rythmicity of the sinus node arising mainly from diminished vagal tonus or stimulation of the sympathetic nerves. Instances of such sinus tachycardia are found, for example, in cases of hyperthyroidism and hyposympathicotonic states in which reduction of the heart-rate is highly desirable for the health of the patient. It is evident, therefore, that a compound which is capable of effectively combating tachycardia constitutes a valuable addition to the therapeutic agents available to the physician for the treatment of pathological or otherwise abnormal heart conditions.

Amongst the drugs commonly used with a view to reducing tachycardia, the β-receptor-blocking agents can be cited. However, these products diminish the supply of oxygen to the cardiac muscle and decrease cardiac performance, which is likely to cause undesirable side-effects such as cardiac decompensation and depression.

The compounds of the invention, on the contrary, as they do not possess cardio-depressant properties, will be devoid of such undesirable side-effects and will, therefore, constitute an appreciable progress compared to the blocking agents in question.

In the field of angina pectoris, it has been observed as reported by R. CHARLIER in the Nouvelle Presse Médicale, 1974, 3, pp. 2407–2410, that, clinically, the cardio-vascular system of the anginal patient presents the following deficiencies:

(1) The myocardium of the anginal subject consumes too much oxygen during an attack of angina pectoris in comparison with the normal subject.
(2) The flow of blood to the myocardium is reduced in the anginal subject in comparison with the normal subject.
(3) The attack of angina pectoris is provoked in more than 95% of cases by an overall stimulation of the sympathetic nervous system.
(4) The performance of the cardiac muscle is depressed with respect to its haemodynamic role i.e. cardiac output both during the attack and at rest.

In view of the above-cited clinical data, it is logical to require that an anti-anginal agent be capable of rectifying or at least alleviating all these disturbances of the haemodynamic functions which are characteristic of the anginal syndrome.

It has been observed that compounds of the invention conform to such criteria.

Therefore, such compounds of the present invention will be amongst the most useful agents for combating angina pectoris and for the long-term treatment of anginal states.

Amongst the compounds of the invention which have shown the most outstanding anti-anginal potentialities, the following compound may be more particularly cited:

2-ethyl-3-[4-(3-di-n-butylaminopropoxy)-benzoyl]-indolizine in the form of the free base or of a pharmaceutically acceptable acid addition salt such as, for example, the hydrochloride or the methanesulphonate. This compound will be hereinafter referred to as Compound A. Pharmacological tests have shown that this Compound A presents the complete range of properties required to rectify or alleviate the four essential deficiencies which characterize the anginal syndrome. Thus, Compound A is capable of:

reducing the consumption of oxygen by the myocardium since it simultaneously decreases cardiac frequency and arterial blood pressure increasing the flow of blood to the heart-muscle exerting anti-adrenergic properties which are characterized by a partial inhibition of the haemodynamic disturbances induced by the stimulation of the α- and β- receptors i.e. hypertension, tachycardia and increase in the oxygen requirements of the myocardium avoiding depression of the cardiac function but, on the contrary, of temporarily stimulating it.

Amongst the agents which are currently used and which present the qualities required for combating angina pectoris and for the long-term treatment of anginal states 2-n-butyl-3-(3,5-diiodo-4-β-N-diethylaminoethoxy-benzoyl)-benzofuran, also known as amiodarone, can be cited. This compound is of undeniable value in the field of angina pectoris.

Comparative tests carried out with Compound A and amiodarone have revealed that, in certain respects, Compound A can be considered as superior to amiodarone, for example with regard to the reduction of the oxygen consumption of the myocardium.

As mentioned above, compounds of the invention have also been found to be valuable anti-arrhythmic agents.

Pharmacological tests have demonstrated that such compounds are capable of suppressing or preventing various experimental types of arrhythmia, for example:

(a) Multifocal ventricular ectopic beats induced by the intravenous injection of epinephrine or of barium chloride in an anaesthetized dog;
(b) Ventricular extrasystoles occurring after ligation of the anterior interventricular coronary artery in an anaesthetized dog;

(c) Auricular fibrillation induced in an anaesthetized dog by application of a solution of acetylcholine to the anterior wall of the right atrium;

(d) Ventricular tachycardia induced either by placing a crystal of aconitine nitrate on the anterior wall of the right ventricle in an anaesthezited dog, or by the intravenous injection of a large dose of strophantine in a morphinized or anaesthetized dog.

As an anti-arrhythmic agent, Compound A, in the form of the free base or of a pharmaceutically acceptable acid addition salt, constitutes the preferred compound for use in this indication.

In the course of pharmacological trials undertaken with compounds of the invention, comparative tests were carried out with Compound A and amiodarone, which is well known for its anti-arrhythmic properties.

The results of such trials in dogs have shown that the effective dose of Compound A against arrhythmia provoked by strophantine, barium chloride, aconitine nitrate, acetylcholine or by ligation of the anterior interventricular coronary artery was from 5 to 10 mg/kg by intravenous route, while the effective dose of amiodarone was 10 mg/kg.

Similarly, in the case of ventricular extrasystoles induced in dogs by epinephrine, the effective dose of Compound A was 2 mg/kg by intravenous route, while the effective dose of amiodarone was from 3 to 5 mg/kg.

The results of pharmacological tests carried out in order to determine the bradycardic, anti-anginal and anti-arrhythmic properties of the compounds of the invention are given hereunder.

I. Bradycardic Properties

Using normal dogs previously anaesthatized, the bradycardic effect was demonstrated after administration of an intravenous dose of 10 mg/kg of the compound under study and the resulting reduction in cardiac frequency was noted in terms of a percentage of the initial heart-rate. The compounds tested in accordance with this procedure were the following, these being preferably used in the form of their hydrochloride or oxalate.

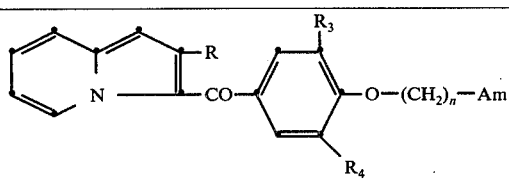

| R | $R_3$ and $R_4$ | n | Am | Reduction of cardiac frequency (in %) |
|---|---|---|---|---|
| Dose : 10 mg/kg | | | | |
| Methyl | hydrogen | 3 | di-n-propylamino | 31 |
| methyl | hydrogen | 3 | di-n-butylamino- | 33 |
| ethyl | hydrogen | 3 | di-n-propylamino | 29 |
| ethyl | hydrogen | 3 | di-n-butylamino | 37 |
| n-propyl | hydrogen | 3 | dimethylamino | 12 |
| n-propyl | hydrogen | 3 | diethylamino | 35 |
| n-propyl | hydrogen | 3 | di-n-propylamino | 28 |
| n-propyl | hydrogen | 3 | di-n-butylamino | 34 |
| isopropyl | hydrogen | 3 | dimethylamino | 20 |
| n-butyl | hydrogen | 3 | diethylamino | 27 |
| n-butyl | hydrogen | 3 | di-n-propylamino | 32 |
| n-butyl | hydrogen | 3 | di-n-butylamino | 28 |
| n-pentyl | hydrogen | 3 | di-n-propylamino | 30 |
| ethyl | hydrogen | 2 | di-n-propylamino | 27 |
| ethyl | hydrogen | 5 | di-n-propylamino | 26 |
| ethyl | hydrogen | 5 | di-n-butylamino | 39 |
| ethyl | hydrogen | 6 | di-n-propylamino | 23 |
| ethyl | hydrogen | 4 | di-n-propylamino | 36 |
| ethyl | hydrogen | 4 | di-n-butylamino | 40 |
| ethyl | hydrogen | 2 | di-n-butylamino | 12 |
| phenyl | hydrogen | 3 | di-n-propylamino | 35 |
| phenyl | hydrogen | 3 | di-n-butylamino | 23 |
| 4-fluoro-phenyl | hydrogen | 3 | dimethylamino | 15 |
| 4-fluoro-phenyl | hydrogen | 3 | diethylamino | 33 |
| 4-methoxy-phenyl | hydrogen | 3 | di-n-propylamino | 27 |
| 4-bromo-phenyl | hydrogen | 3 | dimethylamino | 29 |
| 4-methoxy-phenyl | hydrogen | 3 | dimethylamino | 30 |
| 4-methoxy-phenyl | hydrogen | 3 | di-n-butylamino | 35 |
| 2-bromo-phenyl | hydrogen | 3 | dimethylamino | 35 |
| 3,4-dichloro-phenyl | hydrogen | 3 | di-n-propylamino | 43 |
| methyl | methyl | 3 | diethylamino | 23 |
| methyl | methyl | 3 | di-n-propylamino | 18 |
| methyl | methyl | 3 | di-n-butylamino | 30 |
| ethyl | methyl | 3 | diethylamino | 18 |
| ethyl | methyl | 3 | di-n-propylamino | 28 |
| ethyl | methyl | 3 | di-n-butylamino | 32 |
| n-propyl | methyl | 3 | di-n-propylamino | 29 |
| n-propyl | methyl | 3 | di-n-butylamino | 37 |
| n-butyl | methyl | 3 | di-n-propylamino | 29 |
| Dose : 8.8 mg/kg | | | | |
| phenyl | hydrogen | 3 | diethylamino | 34 |
| Dose : 8.2 mg/kg | | | | |
| 4-chloro-phenyl | hydrogen | 3 | di-n-butylamino | 37 |
| Dose : 6.7 mg/kg | | | | |
| 4-chloro-phenyl | hydrogen | 3 | diethylamino | 34 |
| Dose : 6.4 mg/kg | | | | |
| 4-bromo-phenyl | hydrogen | 3 | di-n-butylamino | 24 |
| Dose : 5 mg/kg | | | | |
| ethyl | hydrogen | 4 | di-n-butylamino | 35 |
| phenyl | hydrogen | 3 | dimethylamino | 17 |
| 4-methoxy-phenyl | hydrogen | 3 | di-n-propylamino | 27 |
| 3,4-dichloro-phenyl | hydrogen | 3 | diethylamino | 27 |
| Dose : 4.6 mg/kg | | | | |
| 4-bromo-phenyl | hydrogen | 3 | di-n-propylamino | 29 |
| Dose : 4.1 mg/kg | | | | |
| 4-chloro-phenyl | hydrogen | 3 | di-n-propylamino | 27 |
| Dose : 2.5 mg/kg | | | | |
| 4-fluoro-phenyl | hydrogen | 3 | di-n-butylamino | 31 |

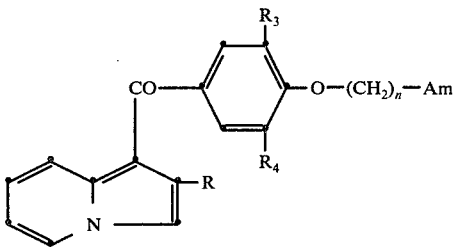

| | | | | |
|---|---|---|---|---|
| Dose : 10 mg/kg | | | | |
| ethyl | hydrogen | 3 | di-n-propylamino | 19 |
| ethyl | hydrogen | 3 | di-n-butylamino | 30 |
| n-propyl | hydrogen | 3 | di-n-propylamino | 29 |
| n-butyl | hydrogen | 3 | di-n-butylamino | 12 |
| ethyl | methyl | 3 | di-n-propylamino | 20 |
| ethyl | methyl | 3 | di-n-butylamino | 25 |

Anti-anginal Properties (1) Intrinsic and anti-adrenergic properties

A first series of four tests was carried out which already suffice to enable a selection to be made of the compounds which are likely to be useful for the treatment of pathological heart conditions and in particular angina pectoris. These tests bear hereinafter the references A, B, C and D. Tests A and B aimed at determining the intrinsic properties of the compounds to be studied with respect to the normal heart of the animal and Tests C and D aimed at evaluating the anti-adrenergic properties of these compounds.

Test A

A dose of the compound to be studied was administered intravenously to a normal dog for the purpose of reducing cardiac frequency. The reduction in cardiac frequency was noted in terms of a percentage of the initial heart-rate.

Test B

The purpose of this test was to determine the reduction in arterial blood-pressure obtained by the intravenous administration to a normal dog of a dose of the compound under study. The reduction in arterial blood-pressure was recorded as a percentage of the initial pressure.

Test C

The purpose of this test was to determine the percentage by which a dose of the compound under study reduced the isoprenaline-accelerated heart-rate in a dog which had previously received an intravenous dose of 1 mg/kg of atropine sulphate. The difference between the maximum accelerated heart-rate and the initial heart-rate was noted and expressed as a percentage of the latter. This percentage, for purposes of convenience, is referred to as X. After the effects of the isoprenaline had disappeared, a dose of the compound to be tested was administered intravenously. The animal then received the same quantity of isoprenaline as before and it was observed that the degree of maximum acceleration in cardiac frequency was less than that previously recorded. This new difference was noted and converted to a percentage of the heart-rate figure recorded before the second administration of isoprenaline. This latter percentage is referred to herein as Y. Finally, Y was subtracted from X and the result was registered as a percentage of X.

Test D

The purpose of this test was to determine the capacity of the compounds under study to reduce epinephrine-increased blood-pressure in the dog which had also previously received an intravenous dose of 1 mg/kg of atropine sulphate. The same procedure was followed as in Test C with regard to the calculation of the percentage of pressure-reduction obtained.

In accordance with the procedures hereabove described, the following compounds of the invention were studied, preferably in the form of their hydrochloride or oxalate and the results obtained are given hereunder:

2-Ethyl-3-[4-(3-di-n-butylaminopropoxy)-benzoyl]-indolizine (Compound A)

2-n-Propyl-3-[4-(3-di-n-propylaminopropoxy)-benzoyl]-indolizine (Compound B)

2-n-Propyl-3-[4-(3-di-n-butylaminopropoxy)-benzoyl]-indolizine (Compound C)

2-n-Butyl-3-[4-(3-di-n-propylaminopropoxy)-benzoyl]-indolizine (Compound D)

2-n-Butyl-3-[4-(3-di-n-butylaminopropoxy)-benzoyl]-indolizine (Compound E)

2-Ethyl-3-[4-(4-di-n-propylaminobutoxy)-benzoyl]-indolizine (Compound F)

2-Ethyl-3-[4-(4-di-n-butylaminobutoxy)-benzoyl]-indolizine (Compound G)

2-Ethyl-3-[4-(3-di-n-butylaminopropoxy)-3,5-dimethyl-benzoyl]-indolizine (Compound H)

2-Ethyl-1-[4-(3-di-n-butylaminopropoxy)-3,5-dimethyl-benzoyl]-indolizine (Compound I)

2-n-Pentyl-3-[4-(3-di-n-butylaminopropoxy)-benzoyl]-indolizine (Compound J)

2-(4-Chloro-phenyl)-3[4-(3-di-n-propylaminopropoxy)-benzoyl]-indolizine (Compound K)

2-(4-Bromo-phenyl)-3-[4-(3-di-n-butylaminopropoxy)-benzoyl]-indolizine (Compound L)

2-(4-Bromo-phenyl)-3-[4-(3-diethylaminopropoxy)-benzoyl]-indolizine (Compound M)

2-(4-Fluoro-phenyl)-3-[4-(3-di-n-propylaminopropoxy)-benzoyl]-indolizine (Compound N)

2-(2-Bromo-phenyl)-3-[4-(3-di-n-butylaminopropoxy)-benzoyl]-indolizine (Compound P)

2-(2-Bromo-phenyl)-3-[4-(3-di-n-propylaminopropoxy)-benzoyl]-indolizine (Compound Q)

2-(2-Bromo-phenyl)-3-[4-(3-diethylaminopropoxy)-benzoyl]-indolizine (Compound R)

2-(3,4-Dichloro-phenyl)-3-[4-(3-di-n-butylaminopropoxy)-benzoyl]-indolizine (Compound S)

2-(3,4-Dichloro-phenyl)-3-[4-(3-dimethylaminopropoxy)-benzoyl]-indolizine (Compound T)

| Compound | Dose (mg/kg) | Test A | Test B | Test C | Test D |
|---|---|---|---|---|---|
| A | 10 | 40 | 20 | 50 | 50 |
| B | 10 | 40 | 20 | 50 | 50 |
| C | 10 | 35 | 20 | 40 | 50 |
| D | 10 | 40 | 20 | 40 | 40 |
| E | 10 | 40 | 20 | 40 | 50 |
| F | 10 | 40 | 20 | 40 | 40 |
| G | 5 | 40 | 20 | 40 | 50 |
| H | 10 | 30 | 20 | 40 | 40 |
| I | 10 | 30 | 20 | 40 | 40 |
| J | 5 | 30 | 20 | 40 | 50 |
| K | 4.1 | 30 | 20 | 40 | 30 |
| L | 2 | 35 | 20 | 30 | 30 |
| M | 10 | 40 | 20 | 15 | 50 |
| N | 10 | 20 | 20 | 40 | 50 |
| P | 10 | 30 | 20 | 50 | 50 |
| Q | 2.5 | 40 | 20 | 50 | 15 |
| R | 5 | 35 | 20 | 50 | 50 |
| S | 10 | 40 | 20 | 50 | 50 |
| T | 10 | 25 | 20 | 15 | 15 |

Further trials were undertaken with Compound A in comparison with amiodarone.

In carrying out these trials, both Compound A and amiodarone were administered intravenously in a dose of 10 mg/kg. In both cases a 5% aqueous solution of the hydrochloride salt was used and the injection took 2 minutes.

(2) Effect on the consumption of oxygen by the myocardium

This property was measured by the indirect method known as the "double-product". This "double-product" is obtained by multiplying the mean systemic systolic arterial blood-pressure by the number of heart-beats per minute. This provides an index of the total amount of oxygen used by the myocardium over a period of one minute. As this index represents an accurate indication of the oxygen consumption of the myocardium, any lowering of the said "double-product" indicates a corresponding drop in the oxygen consumption of the myocardium.

The validity of this system of measurement has been studied by MONROE [Circul. Res., 14, 294 (1964)] KITAMURA et al. [Circulation, 42, 173 (1970)] and ROBINSON [Circulation, 35, 1073 (1967)]. The test was carried out on dogs which had been previously anaesthetized with 30 mg/kg of pentobarbital by intravenous route and intubated with a tracheal cannula. The method used to measure the requisite parameters was that described by R. CHARLIER and J. BAUTHIER in Arzneimittel-Forschung "Drug Research" 23, no. 19, 1305–1311 (1973).

The results obtained in this particular test show that Compound A exerts a markedly superior effect as a reducer of the oxygen consumption of the myocardium than that obtained with amiodarone the comparative results being as follows:

| Intervals of measurement | Oxygen consumption | |
|---|---|---|
| | Compound A | Amiodarone |
| Before administration of the product | 100 | 100 |
| 2.5 min. after administration | 32.5 | 80.9 |
| 5 min. after administration | 40.3 | 79.1 |
| 10 min. after administration | 53.3 | 81.7 |
| 15 min. after administration | 56.6 | 79.7 |
| 20 min. after administration | 59.2 | 79.6 |
| 25 min. after administration | 60.6 | 80.4 |
| 30 min. after administration | 61.7 | 80.2 |
| 35 min. after administration | 62.8 | 79.6 |
| 40 min. after administration | 63.6 | 79.6 |
| 45 min. after administration | 64.8 | 79.6 |
| 50 min. after administration | 66.1 | 80.9 |
| 55 min. after administration | 66.9 | 80.0 |
| 60 min. after administration | 67.7 | 79.1 |

(3) Effect on blood-flow to the myocardium

This test was carried out in order to determine the capability of Compound A and of amiodarone of increasing the blood-flow to the myocardium and thus stepping up the supply of oxygen to this muscle.

It was carried out in accordance with the technique described by R. CHARLIER and J. BAUTHIER in the above-cited Arzneimittel-Forschung "Drug-Research" reference.

The test was undertaken on dogs which received the substance under study in a dose of 10 mg/kg by intravenous route.

It was found that the effect of Compound A was far superior to that of amiodarone 1 minute after administration, the increase in blood-flow to the myocardium being 123% in the case of Compound A and 36% in the case of amiodarone.

(4) Cardiodepressant effect

Tests carried out on dogs have shown that, 90 seconds after the intravenous injection of 10 mg/kg of Compound A, cardiac output was increased by 74% while the same dose of amiodarone in similar conditions increased cardiac output by only 25%.

With respect to systolic output, an increase of 160% was registered 90 seconds after administration of 10 mg/kg of Compound A by intravenous route while the same dose of amiodarone in the same conditions only increased the systolic output by 48%. These results show that neither Compound A nor amiodarone possesses cardiodepressant properties, Compound A being even superior to amiodarone as regards increasing cardiac and systolic output.

III Anti-arrhythmic Properties

The anti-arrhythmic properties of Compound A were tested following different procedures.

In these tests, the arrhythmia-provoking agents were barium chloride, norepinephrine, strophantine and acetylcholine.

Ventricular extrasystoles were provoked, in the anaesthetized dog, by an intravenous injection of 5 mg/kg of barium chloride following the technique of VAN DONGEN (Arch. Int. Pharmacodyn, 1936, 53, 80–88).

Ninety seconds after the end of this injection, an intravenous dose of 5 mg/kg of Compound A was administered within a period of 60 seconds.

It was observed that, at the end of the injection, the rhythm was again normal and it remained so during at least 3 hours.

A marked improvment was also registered after the injection of a dose as low as 2.5 mg/kg of Compound A.

A comparison made with amiodarone showed that the sinus rhythm was also re-established at the end of the injection of 10 mg/kg of this compound. However the effect had disappeared after 4 minutes.

A similar test was also carried out using 0.01 mg/kg of norepinephrine in place of barium chloride. This dose provoked ventricular extrasystoles for 3 minutes. When the rhythm returned spontaneously to normal, an intravenous injection of 2 mg/kg of Compound A was administered over a period of 30 seconds.

The same dose of norepinephrine was then administered 10, 20, 30 and 60 minutes after Compound A. The protective effect of Compound A was complete since the norepinephrine no longer affected the sinus rhythm.

The same test was carried out with 0.005 mg/kg of norepinephrine and 2 mg/kg of amiodarone. Ten minutes after the injection of amiodarone, the second dose of 0.005 mg/kg of norepinephrine was administered. The rhythm which was normal before the second injection of norepinephrine was again upset 45 seconds after this second injection.

When the cardiac rhythm had returned to normal, an additional dose of 5 mg/kg of amiodarone was administered and 10 minutes later a further dose of norepinephrine was injected. This latter dose did not affect the rhythm during the 10 minutes of observation.

Ventricular tachycardia was also produced by injecting an intravenous dose of 0.1 mg/kg of strophantine in the unanaesthetized dog which had previously been treated with 5 mg/kg of morphine by subcutaneous route following the technique of HARRIS (Circulation, 1954, 9, 82).

In this test, the ventricular tachycardia was suppressed with 5 mg/kg of Compound A by intravenous route since sinus rhythm reappeared 12 minutes after the end of the injection and remained for more than 4 hours.

A test of auricular fibrillation induced in the anaesthetized dog by application of a 5%-solution of acetylcholine on the anterior wall of the right atrium was also undertaken following the technique of SCHERF et al (Proc. Soc. Exp. Biol. and Med., 1950 a, 73, 650). An intravenous injection of 10 mg/kg of Compound A administered in 2 minutes re-established sinus rhythm after 6 minutes which remained unchanged for at least 20 minutes even after two further applications of acetylcholine 15 to 17 minutes after the injection of Compound A.

In a similar test carried out with 10 mg/kg of amiodarone normal rhythm did not reappear until 8 minutes after the injection. All of these results taken together show that Compound A can be regarded as superior to amiodarone as an anti-arrhythmic agent.

IV. Toxicity

A comparison was made between the anti-arrhythmic and the arrhythmic doses of both Compound A and amiodarone.

It was found that the arrhythmic dose of Compound A was 63 mg/kg by intravenous route in dogs while that of amiodarone was 83 mg/kg.

However, Compound A is superior to amiodarone with regard to the safety margin between the anti-arrhythmic and the arrhythmic doses.

The dose of Compound A which is active against ventricular extrasystoles induced in dogs by epinephrine is, in fact, 2 mg/kg by intravenous route while the mean dose of amiodarone in this case is 4 mg/kg.

A comparison between the anti-arrhythmic and arrhythmic doses of both compounds shows that the arrhythmic dose, in the case of Compound A, is 31 times greater than the anti-arrhythmic dose while the arrhythmic dose of the amiodarone is only 20.7 times greater than the mean anti-arrhythmic dose.

With respect to the mean anti-arrhythmic dose of Compound A against arrhythmia provoked by strophantine, barium chloride, aconitine nitrate, acetylcholine or by ligation of the anterior interventricular coronary artery, namely 7.5 mg/kg by intravenous route in dogs, it can be seen that the arrhythmic dose is 8.4 times greater while the arrhythmic dose of amiodarone is 8.3 times greater than the anti-arrhythmic dose i.e. 10 mg/kg.

It will be appreciated that for therapeutic use the compounds of the invention will normally be administered in the form of a pharmaceutical or veterinary composition, which may be in a dosage unit form appropriate to the desired mode of administration.

Thus the pharmaceutical or veterinary composition may be in a dosage unit form suitable for oral administration, for example, a coated or uncoated tablet, a hard- or soft-gelatin capsule, a packaged powder, a suspension or a syrup. The composition may alternatively take the form of a suppository for rectal administration, or of a solution or suspension for parenteral administration.

When in dosage unit form, the composition may contain for example from 15% to 50% by weight of the active ingredient per dosage unit for oral administration, from 3% to 15% of the active ingredient per dosage unit for rectal administration and from 3% to 5% of active ingredient per dosage unit for parenteral administration.

Irrespective of the form which the composition takes, the pharmaceutical or veterinary composition of the invention will normally be prepared by associating at least one of the compounds of formula I or a pharmaceutically acceptable acid addition salt thereof with an appropriate pharmaceutical carrier or excipient therefor, for example, one or more of the following substances: milk sugar, starches, talc, magnesium stearate, polyvinylpyrrolidone, alginic acid, colloidal silica, distilled water, benzyl alcohol or flavouring agents.

In order to obtain the best possible resorption in the subject to be treated, the compounds of the invention, when used by oral route, will be, preferably, administered together with an agent capable of modifying the level of gastric secretions, for example by stimulating these secretions and/or diluting gastric acidity. Such an agent can be food, for example fatty meat, carbohydrates or even autoemulsifying oils or fats having hydrosoluble and liposoluble properties except those having either a liposoluble or a hydrosoluble property which is considerably greater than the other. As autoemulsifying oils useful in the present case, polyoxyethylene oleic triglycerides can be cited.

The following Examples illustrate the invention:

EXAMPLE 1

2-Ethyl-3-[4-(3-di-n-butylaminopropoxy)-benzoyl]-indolizine and salts thereof (a) 1-Ethoxycarbonylmethyl-2-methyl-pyridinium chloride In a 4-liter flask, a mixture of 372 g (4 mols) of 2-picoline and 493.2 g (4 mols) of ethyl chloroacetate in 2 l of isopropanol was refluxed for 20 hours. At the end of the reaction, the solvent was evaporated off and the residue was ground with acetone and placed in a refrigerator. It was subsequently suction-filtered and dried.

By this method, 662 g of 1-ethoxycarbonylmethyl-2-methylpyridinium chloride were obtained, which represents a yield of 76.5%

M.P. 120°–121° C.

(b) 2-Ethyl-indolizine

In a 20-liter flask, a mixture of 1620 g (7.5 mols) of 1-ethoxycarbonylmethyl-2-methyl-pyridinium chloride, 10 l (7.5 mols) of propionic anhydride and 1850 g (22.5 mols) of anhydrous sodium acetate was refluxed for 20 hours. At the end of the reaction, the excess of anhydride was distilled off under vacuum and the residue taken up in 7.5 l of water. The solution was neutralized with sodium carbonate, extracted with benzene and washed with water.

The solvent was then evaporated off and the residue was heated under reflux for 2 hours with 3 l of concentrated hydrochloric acid. The mixture was cooled, neutralized with a 30%- sodium hydroxide solution and the product so obtained was suction-filtered at 10° C. After drying, the product was distilled off at a temperature of 126°–128° C and under 15 mm Hg.

By this method, 828 g of 2-ethyl-indolizine were obtained, which represents a yield of 76.2%.

M.P. 42°–44° C

Following the procedure described above but using the appropriate starting-products, the compounds listed hereunder were prepared:

| Compound | Boiling point ° C |
| --- | --- |
| 2-Methyl-indolizine | 130 |
| | (15 mm Hg) |
| | M.P. 61–62° C |
| 2-n-Propyl-indolizine | 143–150 |
| | (15 mm Hg) |
| 2-Isopropyl-indolizine | 136–138 |
| | (15 mm Hg) |
| | M.P. 46–47° C |
| 2-n-Butyl-indolizine | 77–90 |
| | (0.001 mm Hg) |
| 2-n-Pentyl-indolizine | 90–93 |
| | (0.01 mm Hg) |

(c) 2-Ethyl-3-(4-tosyloxy-benzoyl)-indolizine

In a 4-liter flask containing a solution of 411 g (2.83 mols) of 2-ethyl-indolizine in 2500 ml of benzene, 965 g (3.11 mols) of 4-tosyloxy-benzoyl chloride i.e. 4-p-toluenesulphonyl-benzoyl chloride, were added at a temperature of 15° to 20° C. The mixture was stirred for 12 hours and then poured into a solution of 5600 g of potassium carbonate in 8000 ml of water.

The mixture was stirred for one hour and the solid product which formed was suction-filtered which gave the first fraction of the desired compound.

The benzene phase was decanted out, washed with water to neutrality and the solvent was evaporated off. A second fraction of the desired product was thus obtained.

By this method, a total of 1050 g of 2-ethyl-3-(4-tosyloxy-benzoyl)-indolizine was obtained, which represents a yield of 88%.

M.P. 165° C.

Following the procedure described above but using the appropriate starting-products, the compounds listed hereunder were prepared:

| Compound | Melting point ° C |
|---|---|
| 2-Methyl-3-(4-tosyloxy-benzoyl)-indolizine | 171–172 (benzene) |
| 2-n-Propyl-3-(4-tosyloxy-benzoyl)-indolizine | 112–114 (ethanol) |
| 2-Isopropyl-3-(4-tosyloxy-benzoyl)-indolizine | 146–147 (isopropanol) |
| 2-n-Butyl-3-(4-tosyloxy-benzoyl)-indolizine | 94–95 (ethanol/water) |
| 2-n-Pentyl-3-(4-tosyloxy-benzoyl)-indolizine | 95–96 (methanol) |
| 2-Methyl-3-(4-tosyloxy-3,5-dimethyl-benzoyl)-indolizine | 184–186 (dichlorethane) |
| 2-Ethyl-3-(4-tosyloxy-3,5-dimethyl-benzoyl)-indolizine | 87–88 (methanol) |
| 2-n-Propyl-3-(4-tosyloxy-3,5-dimethyl-benzoyl)-indolizine | oil - used in crude form |
| 2-Isopropyl-3-(4-tosyloxy-3,5-dimethyl-benzoyl)-indolizine | 136–137 (isopropanol) |
| 2-n-Butyl-3-(4-tosyloxy-3,5-dimethyl-benzoyl)-indolizine | oil - used in crude form |

(d) 2-Ethyl-3-(4-hydroxy-benzoyl)-indolizine

In a 20-liter flask, a suspension of 1050 g (2.5 mols) of 2-ethyl-3-(4-tosyloxy-benzoyl)-indolizine in a solution of 420 g (10.5 mols) of sodium hydroxide dissolved in 8 l of ethanol and 4 l of water was refluxed for 6 hours. At the end of the reaction, the mixture was cooled, diluted with 2.5 l of water, neutralized with hydrochloric acid and the desired product was allowed to crystallize while being stirred. The product was then suction-filtered and dried under vacuum in a drying-oven maintained at 70° C.

By this method, 560 g of 2-ethyl-3-(4-hydroxy-benzoyl)-indolizine were obtained, which represents a yield of 84.5%.

M.P. 179°–180° C.

Following the procedure described above but using the appropriate starting-products, the compounds listed hereunder were prepared:

| Compound | Melting point ° C |
|---|---|
| 2-Methyl-3-(4-hydroxy-benzoyl)-indolizine | 209–210 (2/1 ethanol/water) |
| 2-n-Propyl-3-(4-hydroxy-benzoyl)-indolizine | 153–155 (methanol) |
| 2-Isopropyl-3-(4-hydroxy-benzoyl)-indolizine | 162–163.5 (methanol/ethanol) |
| 2-n-Butyl-3-(4-hydroxy-benzoyl)-indolizine | 142–143 (ethanol/water) |
| 2-n-Pentyl-3-(4-hydroxy-benzoyl)-indolizine | 125–126 (carbon tetrachloride) |
| 2-Methyl-3-(4-hydroxy-3,5-dimethyl-benzoyl)-indolizine | 219 (methanol) |
| 2-Ethyl-3-(4-hydroxy-3,5-dimethyl-benzoyl)-indolizine | 165–167 (carbon tetrachloride) |
| 2-n-Propyl-3-(4-hydroxy-3,5-dimethyl-benzoyl)-indolizine | 167–169 (isopropanol) |
| 2-Isopropyl-3-(4-hydroxy-3,5-dimethyl-benzoyl)-indolizine | 184–185 (isopropanol) |
| 2-n-Butyl-3-(4-hydroxy-3,5-dimethyl-benzoyl)-indolizine | 167–168 (isopropanol) |

(e) 2-Ethyl-3-[4-(3-bromo-propyl)-oxy-benzoyl]-indolizine

In a 2-liter flask, a mixture of 98.5 g (0.37 mol) of 2-ethyl-3-(4-hydroxy-benzoyl)-indolizine, 103.5 g (0.74 mol) of potassium carbonate and 770 ml of acetone was stirred for 30 minutes. To this reaction medium 370 g (1.85 mol) of 1,3-dibromo-propane were then added and the mixture was refluxed for 6 hours.

After cooling, the mineral salts were filtered out and washed with acetone. The acetone was evaporated off and the residue was added to 700 ml of petroleum ether (40°–60° C). One part of the residue crystallized while the other part formed a slightly soluble oil. In this way, a first fraction of 18.6 g of the desired product in crystal form was obtained, melting at 70°–71° C. The undissolved oil was then recrystallized from 350 ml of methanol which provided a second fraction representing 92.1 g of the desired product melting at 68°–70° C.

By this method, 2-ethyl-3-[4-(3-bromo-propyl)-oxy-benzoyl]-indolizine was obtained with a total yield of 77.6%.

Following the procedure described above but using the appropriate starting-products, the compounds listed hereunder were prepared:

| Compound | Melting point ° C |
|---|---|
| 2-Methyl-3-[4-(3-bromo-propyl)-oxy-benzoyl]-indolizine | 104–105 (benzene/petroleum ether 50–75°) |
| 2-Ethyl-3-[4-(2-bromo-ethyl)-oxy-benzoyl]-indolizine | 77–78 (petroleum ether 40–60°) |
| 2-Ethyl-3-[4-(4-bromo-butyl)-oxy-benzoyl]-indolizine | 68–69 (methanol) |
| 2-Ethyl-3-[4-(5-bromo-pentyl)-oxy-benzoyl]-indolizine | oil - used in crude form |
| 2-Ethyl-3-[4-(6-bromo-hexyl)-oxy-benzoyl]-indolizine | oil - used in crude form |
| 2-n-Propyl-3-[4-(3-bromo-propyl)-oxy-benzoyl]-indolizine | 71–72 (petroleum ether 50–75°) |
| 2-Isopropyl-3-[4-(3-bromo-propyl)-oxy-benzoyl]indolizine | oil - used in crude form |
| 2-n-Butyl-3-[4-(3-bromo-propyl)-oxy-benzoyl]-indolizine | 76–77 (petroleum ether 50–75°) |
| 2-n-Pentyl-3-[4-(3-bromo-propyl)-oxy benzoyl]-indolizine | oil - used in crude form |
| 2-Methyl-3-[4-(3-bromo-propyl)-oxy-3,5-dimethyl-benzoyl]-indolizine | 108 (cyclohexane) |
| 2-Ethyl-3-[4-(3-bromo-propyl)-oxy-3,5-dimethyl-benzoyl-]-indolizine | 69–72 (ethanol) |
| 2-n-Propyl-3-[4-(3-bromo-propyl)-oxy-3,5-dimethyl-benzoyl]-indolizine | 65.5–68 (ethanol) |
| 2-Isopropyl-3-[4-(3-bromo-propyl)-oxy-3,5-dimethyl-benzoyl]-indolizine | oil - used in crude form |
| 2-n-Butyl-3-(4-(3-bromo-propyl)-oxy-3,5-dimethyl-benzoyl]-indolizine | oil - used in crude form |

(f) 2-Ethyl-3-[4-(3-di-n-butylaminopropoxy)-benzoyl]-indolizine

In a 3-liter flask, a solution of 159 g (0.41 mol) of 2-ethyl-3-[4-(3-bromo-propyl)-oxy-benzoyl]-indolizine, 159 g (1.23 mol) of N,N-di-n-butylamine and 1650 ml of benzene was refluxed for 3 hours. At the end of the reaction, the reaction medium was allowed to cool, washed with water and the solvent was evaporated off.

By this method, 2-ethyl-3-[4-(3-di-n-butylaminopropoxy)-benzoyl]-indolizine in free base form was obtained.

Following the procedure described above, the compound hereunder was prepared:

| Compound | Melting point ° C of the pure product |
|---|---|
| 2-Isopropyl-3-[4-(3-dimethylaminopropoxy)-benzoyl]-indolizine | 78–79 (isopropyl ether) |

(g) 2-Ethyl-3-[4-(3-di-n-butylaminopropoxy)-benzoyl]-indolizine hydrochloride The crude base, obtained as described above, was purified by reaction with oxalic acid to obtain an oxalate which was then recrystallized from benzene. The base was then isolated from its salt and was dissolved in diisopropyl ether and the hydrochloride was formed by adding a solution of hydrochloric acid in diisopropyl ether.

By this method, 34 g of 2-ethyl-3-[4-(3-di-n-butylaminopropoxy)-benzoyl]-indolizine hydrochloride were obtained after recrystallization from acetone, which represents a yield of 58.5%.

M.P. 112.5°–113.5° C.

Following the procedure described above but using the appropriate starting-products, the compounds listed hereunder were prepared:

| Compound | Melting point ° C |
|---|---|
| 2-Methyl-3-[4-(3-di-n-propylaminopropoxy)-benzoyl]-indolizine hydrochloride | 148–150 (acetone/ethyl acetate) |
| 2-Methyl-3-[4-(3-di-n-butylaminopropoxy)-benzoyl]-indolizine hydrochloride | 115–117 (acetone/ethyl acetate) |
| 2-Ethyl-3-[4-(3-di-n-propylaminopropoxy)-benzoyl]-indolizine hydrochloride | 139–141 (acetone/ethyl acetate) |
| 2-n-Propyl-3-[4-(3-dimethylaminopropoxy)-benzoyl]-indolizine hydrochloride | 152–154 (acetone/ethyl acetate) |
| 2-n-Propyl-3-[4-(3-diethylaminopropoxy)-benzoyl]-indolizine hydrochloride | 133.5–134.5 (acetone/ethyl acetate) |
| 2-n-Propyl-3-[4-(3-di-n-propylaminopropoxy)-benzoyl]-indolizine hydrochloride | 151–153 (acetone/ethyl acetate) |
| 2-n-Propyl-3-[4-(3-di-n-butylaminopropoxy)-benzoyl]-indolizine hydrochloride | 78–80 (ethyl acetate/ether) |
| 2-n-Butyl-3-[4-(3-diethylaminopropoxy)-benzoyl]-indolizine hydrochloride | 139–141 (acetone/ethyl acetate) |
| 2-n-Butyl-3-[4-(3-di-n-propylaminopropoxy)-benzoyl]-indolizine hydrochloride | 159–161 (ethyl acetate) |
| 2-n-Butyl-3-[4-(3-di-n-butylaminopropoxy)-benzoyl]-indolizine hydrochloride | 69.5–71 (ethyl acetate/ether) |
| 2-n-Propyl-3-[4-(3-morpholinopropoxy)-benzoyl]-indolizine hydrochloride | 158–160 (acetone/ethyl acetate) |
| 2-Ethyl-3-[4-(2-di-n-propylaminoethoxy)-benzoyl]-indolizine hydrochloride | 158–161 (acetonitrile) |
| 2-Methyl-3-[4-(3-diethylaminopropoxy)-3,5-dimethyl-benzoyl]-indolizine hydrochloride | 186–188 (acetone) |
| 2-Methyl-3-[4-(3-di-n-propylaminopropoxy)-3,5-dimethyl-benzoyl]-indolizine hydrochloride | 158–160 (acetone) |
| 2-Methyl-3-[4-(3-di-n-butylaminopropoxy)-3,5-dimethyl-benzoyl]-indolizine hydrochloride | 137–138 (acetone) |
| 2-Ethyl-3-[4-(3-diethylaminopropoxy)-3,5-dimethyl-benzoyl]-indolizine hydrochloride | 183–185 (isopropanol) |
| 2-Ethyl-3-[4-(3-di-n-propylaminopropoxy)-3,5-dimethyl-benzoyl]-indolizine hydrochloride | 133.5–135 (acetone) |
| 2-Ethyl-3-[4-(3-di-n-butylaminopropoxy)-3,5-dimethyl-benzoyl]-indolizine hydrochloride | 169–171 (acetonitrile) |
| 2-n-Propyl-3-[4-(3-di-n-propylaminopropoxy)-3,5-dimethyl-benzoyl]-indolizine hydrochloride | 134–136 (acetone) |
| 2-n-Propyl-3-[4-(3-di-n-butylaminopropoxy)-3,5-dimethyl-benzoyl]-indolizine hydrochloride | 154–156 (ethyl acetate) |

(h) 2-Ethyl-3-[4-(3-di-n-butylaminopropoxy)-benzoyl]-indolizine methanesulphonate In a flask, 11.2 g (0.026 mol) of 2-ethyl-3-[4-(3-di-n-butylaminopropoxy)-benzoyl]indolizine were dissolved in 250 ml of isopropanol. To this reaction medium, a solution of 3.4 g (0.025 mol) of methanesulphonic acid in water titrating 69.25% was added. The mixture was stirred for 30 minutes and evaporated to dryness.

The residue so obtained was taken up in 100 ml of isopropanol and the solution was evaporated. These latter operations were effected three times. After that, 200 ml of isopropylether were added to the residue and the mixture was triturated, stirred, decanted and a further 200 ml of isopropylether were added. The mixture was allowed to stand for 12 hours and 13 g of a soft solid were obtained which were crystallized in 90 ml of ethyl acetate by cooling to 0° to −5° C. The crystals were then filtered out.

By this method, 6.5 g of 2-ethyl-3-[4-(3-di-n-butylaminopropoxy)-benzoyl]-indolizine methanesulphonate were obtained. M.P. 51°–53° C.

EXAMPLE 2

2-Ethyl-3-[4-(2-di-n-butylaminoethoxy)-benzoyl]-indolizine acid oxalate

To a solution of 7.7 g (0.018 mol) of 2-ethyl-3-[4-(2-di-n-butylaminoethoxy)-benzoyl]-indolizine base, prepared as in Example 1, in 80 ml of ethyl ether, were added, at room-temperature, 2.8 g (0.022 mol) of oxalic acid in 200 ml of ethyl ether. The acid oxalate which precipitated was suction-filtered, washed with ethyl ether and dried.

By this method, 9.1 g of 2-ethyl-3-[4-(2-di-n-butylaminoethoxy)-benzoyl]-indolizine acid oxalate were obtained after recrystallization from a benzene/dichlorethane mixture. M.P. 115.5°–116.5° C.

Following the procedure described above, the compounds listed hereunder were prepared:

| Compound | Melting point ° C |
|---|---|
| 2-Ethyl-3-[4-(5-di-n-propylaminopentoxy)-benzoyl]-indolizine acid oxalate | 117.5–119 (benzene) |
| 2-Ethyl-3-[4-(5-di-n-butylaminopentoxy)- | 115–116 |

-continued

| Compound | Melting point ° C |
|---|---|
| benzoyl]-indolizine acid oxalate | (benzene) |
| 2-Isopropyl-3-[4-(3-di-n-butylaminopropoxy)-benzoyl]-indolizine acid oxalate ,H₂O | 90-92 (benzene) |
| 2-Ethyl-3-[4-(6-di-n-propylaminohexoxy)-benzoyl]-indolizine acid oxalate | 138-139 (benzene/dichlorethane) |
| 2-Ethyl-3-[4-(4-di-n-propylaminobutoxy)-benzoyl]-indolizine acid oxalate | 114-115 (benzene) |
| 2-Ethyl-3-[4-(4-di-n-butylaminobutoxy)-benzoyl]-indolizine acid oxalate | 92-94 (benzene) |
| 2-n-Pentyl-3-[4-(3-di-n-butylaminopropoxy)-benzoyl]-indolizine acid oxalate | 92-93 (benzene) |
| 2-n-Pentyl-3-[4-(3-di-n-propylaminopropoxy)-benzoyl]-indolizine acid oxalate | 97.5-99 (benzene) |
| 2-n-Butyl-3-[4-(3-di-n-propylaminopropoxy)-3,5-dimethyl-benzoyl]-indolizine acid oxalate | 143 (benzene) |
| 2-n-Butyl-3-[4-(3-di-n-butylaminopropoxy)-3,5-dimethyl-benzoyl]-indolizine acid oxalate. ,H₂O | 90-92 (benzene) |
| 2-Ethyl-3-[4-(6-di-n-butylaminohexoxy)-benzoyl]-indolizine acid oxalate | 95-96 (benzene) |

EXAMPLE 3

2-n-Propyl-3-[4-(3-di-n-butylaminopropoxy)-benzoyl]-indolizine hydrochloride

In a 250-ml flask, a suspension of 10 g (0.036 mol) of 2-n-propyl-3-(4-hydroxy-benzoyl)-indolizine and 9.9 g (0.072 mol) of potassium carbonate in 60 ml of acetone was stirred for 30 minutes. After this operation, 8.8 g (0.040 mol) of 1-chloro-3-di-n-butylaminopropane were added to the reaction medium which was then refluxed for 20 hours. After cooling, the organic salts were filtered out and the solvent was evaporated off. The excess of halogenoamine was distilled off under a vacuum of 0.2 Torr.

The base so obtained was purified by elution chromatography on a column after which is was dissolved in ether and the hydrochloride was formed by adding a solution of hydrochloric acid in ether.

By this method, 1.51 g of 2-n-propyl-3-[4-(3-di-n-butylaminopropoxy)-benzoyl]-indolizine hydrochloride were obtained after recrystallization from a mixture of ethyl acetate and ether, which represents a yield of 68%. M.P. 78°-80° C.

Following the procedure described above, the compounds hereunder were prepared:

| Compound | Melting point ° C |
|---|---|
| 2-Ethyl-3-[4-(3-di-n-butylaminopropoxy)-benzoyl]-indolizine hydrochloride | 113 |
| 2-n-Butyl-1-[4-(3-di-n-butylaminopropoxy)-benzoyl]-indolizine acid oxalate | 81-83 (benzene/dichlorethane) |

EXAMPLE 4

2-n-Propyl-1-[4-(3-di-n-propylaminopropoxy)-benzoyl]-indolizine hydrochloride (a) 3-Acetyl-2-n-propyl-indolizine In a 1-liter flask, a mixture of 68.5 g (0.43 mol) of 2-n-propylindolizine, 404 ml of acetic anhydride and 56.5 g of sodium acetate was heated under reflux for 7 hours. At the end of the reaction, the excess of acetic anhydride was evaporated off under vacuum and then ethanol and water were added to the residue so obtained. The resulting acetylated compound was extracted with dichlorethane and the organic solution was washed with an aqueous solution of sodium hydrogenocarbonate and then with water. The solvent was evaporated off under vacuum and the product so obtained was recrystallized from petroleum ether (40°-60° C).

By this method, 74.5 g of 3-acetyl-2-n-propyl-indolizine were obtained, which represents a yield of 86.2%. M.P. 71°-72° C.

Following the procedure described above but using the appropriate starting-products, the compounds listed hereunder were prepared:

| Compound | Melting point ° C. |
|---|---|
| 3-Acetyl-2-methyl-indolizine | 80 |
| 3-Acetyl-2-ethyl-indolizine | 60-62 (petroleum ether 40-60° |
| 3-Acetyl-2-isopropyl-indolizine | B.P. 110-120° C (0.05 mm Hg) |
| 3-Acetyl-2-n-butyl-indolizine | 61-62 (petroleum ether 40-60°) |

(b) 3-Acetyl-2-n-propyl-1-(4-tosyloxy-benzoyl)-indolizine

In a flask, a solution of 50.3 g (0.25 mol) of 3-acetyl-2-n-propyl-indolizine in 75 ml of dichlorethane was cooled to between 0° and 5° C. After this operation, 66.5 g (0.5 mol) of aluminium chloride were added piecemeal. To this suspension, a solution of 77.6 g (0.25 mol) of 4-tosyloxy-benzoyl chloride in 50 ml of dichlorethane was added, while stirring, and the reaction medium was then allowed to return to room-temperature. Stirring was maintained for 12 hours and the mixture was hydrolyzed with a mixture of 50ml of concentrated hydrochloric acid and 250 g of ice. Stirring was maintained for a further hour after which the mixture was extracted with dichlorethane, washed with an aqueous solution of sodium hydrogenocarbonate and then with water. The solvent was evaporated off under vacuum and the residue was recrystallized from methanol.

By this method, 37 g of 3-acetyl-2-n-propyl-1-(4-tosyloxybenzoyl)-indolizine were obtained, which represents a yield of 31.2%. M.P. 125°-126° C.

Following the procedure described above, but using the appropriate starting-products, the compounds listed hereunder were prepared:

| Compound | Melting point ° C. |
|---|---|
| 3-Acetyl-2-methyl-1-(4-tosyloxy-benzoyl)-indolizine | 150-153 (isopropanol) |
| 3-Acetyl-2-ethyl-1-(4-tosyloxy-benzoyl)-indolizine | 126-127 (carbon tetrachloride) |
| 3-Acetyl-2-isopropyl-1-(4-tosyloxy-benzoyl)-indolizine | 158-160 (methanol) |
| 3-Acetyl-2-n-butyl-1-(4-tosyloxy-benzoyl)-indolizine | 122-123 (carbon tetrachloride) |
| 3-Acetyl-2-ethyl-1-(4-tosyloxy-3,5-dimethyl-benzoyl)-indolizine | 175-176 (carbon tetrachloride) |

(c) 2-n-Propyl-1-(4-tosyloxy-benzoyl)-indolizine

In a flask, a suspension of 30.5 g (0.064 mol) of 3-acetyl-2-n-propyl-1-(4-tosyloxy-benzoyl)-indolizine in 300 ml of concentrated hydrochloric acid was stirred for 5 hours at room-temperature. The solution was diluted with 500 ml of water and the product, which precipitated, was separated by decantation and then recrystallized from methanol.

By this method, 25.1 g of 2-n-propyl-1-(4-tosyloxy-benzoyl)-indolizine were obtained, which represents a yield of 90.3%. M.P. 95°-97° C.

Following the procedure described above but using the appropriate starting-products, the compounds listed hereunder were prepared:

| Compound | Melting point ° C |
| --- | --- |
| 2-Methyl-1-(4-tosyloxy-benzoyl)-indolizine | 143–144 (methanol) |
| 2-Ethyl-1-(4-tosyloxy-benzoyl)-indolizine | 112–113 (methanol) |
| 2-Isopropyl-1-(4-tosyloxy-benzoyl)-indolizine | 121–123 (isopropanol) |
| 2-n-Butyl-1-(4-tosyloxy-benzoyl)-indolizine | 133–134 (isopropanol) |
| 2-Ethyl-1-(4-tosyloxy-3,5-dimethyl-benzoyl)-indolizine | 116–118 (methanol) |

(d) 2-n-Propyl-1-(4-hydroxy-benzoyl)-indolizine

In a flask, a solution of 27 g (0.062 mol) of 2-n-propyl-1-(4-tosyloxy-benzoyl)-indolizine, 10 g (0.25 mol) of sodium hydroxide, 68 ml of water and 34 ml of ethanol was refluxed, while stirring, for 6 hours. At the end of the reaction, the mixture was cooled, acidified with hydrochloric acid and the product so obtained was suctionfiltered and recrystallized from methanol.

By this method 14.4 g of 2-n-propyl-1-(4-hydroxy-benzoyl)-indolizine were obtained, which represents a yield of 83.2%. M.P. 210°–214° C.

Following the procedure described above but using the appropriate starting-products, the compounds listed hereunder were prepared:

| Compound | Melting point ° C |
| --- | --- |
| 2-Methyl-1-(4-hydroxy-benzoyl)-indolizine | 197–200 (methanol) |
| 2-Ethyl-1-(4-hydroxy-benzoyl)-indolizine | 159–160 (dichlorethane) |
| 2-Isopropyl-1-(4-hydroxy-benzoyl)-indolizine | 157–159 (benzene) |
| 2-n-Butyl-1-(4-hydroxy-benzoyl)-indolizine | 186–187 (methanol) |
| 2-Ethyl-1-(4-hydroxy-3,5-dimethyl-benzoyl)-indolizine | 186–187 (methanol) |

(e) 2-n-Propyl-1-[4-(3-bromo-propyl)-oxy-benzoyl]-indolizine

To a suspension of 20 g (0.071 mol) of 2-n-propyl-1-(4-hydroxybenzoyl)-indolizine in 160 ml of anhydrous acetone were added 19.5 g (0.142 mol) of potassium carbonate. The mixture was stirred for 30 minutes and then 36 ml (0.355 mol) of 1,3-dibromo-propane were added. The reaction medium was refluxed for 6 hours after which the solvent was evaporated off under reduced pressure. The residue so obtained was taken up in chloroform, the insoluble salts were filtered out and the solution was evaporated to dryness. The oily residue so obtained was purified by chromatography on a dry column using silica as adsorbent and chloroform as solvent.

By this method 2-n-propyl-1-[4-(3-bromo-propyl)-oxy-benzoyl]-indolizine was obtained in crude form.

Following the procedure described above but using the appropriate starting-products, the compound hereunder was prepared:

| Compound | Melting point ° C |
| --- | --- |
| 2-Ethyl-1-[4(3-bromo-propyl)-oxy- | 87–88 |

-continued

| Compound | Melting point ° C |
| --- | --- |
| 3,5-dimethyl-benzoyl]-indolizine | (methanol) |

(f) 2-n-Propyl-1-[4-(3-di-n-propylaminopropoxy)-benzoyl]-indolizine hydrochloride To a solution of 5 g (0.0125 mol) of 2-n-propyl-1-[4-(3-bromopropyl)-oxy-benzoyl]-indolizine in 60 ml of benzene, were added 5.1 ml (0.0375 mol) of di-n-propylamine. The mixture was refluxed for 20 hours and then washed with water. The benzene phase was evaporated to dryness and the residue so obtained was purified by chromatography on a dry column using silica as adsorbent and ethyl acetate as solvent. The base so purified was dissolved in anhydrous ethyl ether and a solution of hydrochloric acid in ether was then added to precipitate the hydrochloride.

By this method, 2-n-propyl-1-[4-(3-di-n-propylaminopropoxy)-benzoyl]-indolizine hydrochloride was obtained with a yield of 28%. M.P. 126°–129° C.

Following the procedure described above but using the appropriate starting-products, the compounds listed hereunder were prepared:

| Compound | Melting point ° C |
| --- | --- |
| 2-Ethyl-1-[4-(3-di-n-propylamino-propoxy)-benzoyl]-indolizine sesquioxalate | 99.5–104.5 (dichlorethane) |
| 2-Ethyl-1-[4-(3-di-n-butylamino-propoxy)-benzoyl]-indolizine acid oxalate | 83–85 (dichloroethane/benzene) |
| 2-Ethyl-1-[4-(3-di-n-butylamino-propoxy)-3,5-dimethyl-benzoyl]-indolizine acid oxalate | 180 (acetonitrile) |
| 2-Ethyl-1-[4-(3-di-n-propylamino-propoxy)-3,5-dimethyl-benzoyl]-indolizine indolizene acid oxalate | 134–135 dichlorethane) |

EXAMPLE 5

2-Phenyl-3-[4-(3-di-n-butylaminopropoxy)-benzoyl]-indolizine acid oxalate (a) 2-Phenyl-3-(4-tosyloxy-benzoyl)-indolizine In a flask, containing a solution of 6.5g (0.044 mol) of 2-phenylindolizine in 100 ml of dichlorethane, 12.4 g (0.04 mol) of 4-tosyloxy-benzoyl chloride were added at room-temperature. The mixture was stirred for 12 hours and then poured into a 10%-solution of sodium carbonate. The product which precipitated was washed to neutrality and recrystallized from carbon tetrachloride. In this manner, 2-phenyl-3-(4-tosyloxy-benzoyl)-indolizine was obtained in a yield of 52.3%. M.P. 177°–178° C Following the same procedure as that described above but using the appropriate starting-products, the compounds listed hereunder were prepared:

| Compound | Melting point ° C |
| --- | --- |
| 2-(4-Fluoro-phenyl)-3-(4-tosyloxy-benzoyl)-indolizine | 175 (isopropanol) |
| 2-(4-Chloro-phenyl)-3-(4-tosyloxy-benzoyl)-indolizine | 215–217 (dichlorethane) |
| 2-(4-Bromo-phenyl)-3-(4-tosyloxy-benzoyl)-indolizine | 210 (isopropanol) |
| 2-(4-Methoxy-phenyl)-3-(4-tosyloxy-benzoyl)-indolizine | 181 (isopropanol) |
| 2-(2-Bromo-phenyl)-3-(4-tosyloxy-benzoyl)-indolizine | 195 (ethyl acetate) |
| 2-(3,4-Dichloro-phenyl)-3-(4-tosyloxy-benzoyl)-indolizine | 191 (ethyl acetate) |

-continued

| Compound | Melting point ° C |
|---|---|
| 2-(3-Bromo-phenyl)-3-(4-tosyloxy-benzoyl)-indolizine | 131 |
| 2-(3-Chloro-4-methyl-phenyl)-3-(4-tosyloxy-benzoyl)-indolizine | 179 (ethyl acetate) |
| 2-(4-Methyl-phenyl)-3-(4-tosyloxy-benzoyl)-indolizine | 176–179 (carbon tetrachloride) |

(b) 2-Phenyl-3-(4-hydroxy-benzoyl)-indolizine

In a flask, a suspension of 30.8 g (0.066 mol) of 2-phenyl-3-(4-tosyloxy-benzoyl)-indolizine in a solution of 11.2 g (0.28 mol) of sodium hydroxide dissolved in 204 ml of methanol and 102 ml of water was refluxed for 12 hours.

After that, the mixture was cooled and acidified with hydrochloric acid to neutrality. The precipitate so formed was then suctionfiltered.

In this manner, 2-phenyl-3-(4-hydroxy-benzoyl)-indolizine was obtained in a yield of 85.2%. M.P. 179° C.

Following the same procedure as that described above but using the appropriate starting-products, the compounds listed hereunder were prepared:

| Compound | Melting point ° C |
|---|---|
| 2-(4-Fluoro-phenyl)-3-(4-hydroxy-benzoyl)-indolizine | 228 (dichlorethane) |
| 2-(4-Chloro-phenyl)-3-(4-hydroxy-benzoyl)-indolizine | 249–250 (isopropanol) |
| 2-(4-Bromo-phenyl)-3-(4-hydroxy-benzoyl)-indolizine | 253 (methanol) |
| 2-(4-Methoxy-phenyl)-3-(4-hydroxy-benzoyl)-indolizine | 214 (dichlorethane) |
| 2-(2-Bromo-phenyl)-3-(4-hydroxy-benzoyl)-indolizine | 198 (isopropanol) |
| 2-(3,4-Dichloro-phenyl)-3-(4-hydroxy-benzoyl)-indolizine | 207–209 (isopropanol) |
| 2-(3-Bromo-phenyl)-3-(4-hydroxy-benzoyl)-indolizine | 108–110 (isopropanol) |
| 2-(3-Chloro-4-methyl-phenyl)-3-(4-hydroxy-benzoyl)-indolizine | 183 (methanol) |
| 2-(4-Methyl-phenyl)-3-(4-hydroxy-benzoyl)-indolizine | 209–210 (benzene) |

(c) 2-Phenyl-3-[4-(3-di-n-butylaminopropoxy)-benzoyl]-indolizine acid oxalate

In a flask, a mixture of 6.25 g (0.02 mol) of 2-phenyl-3-(4-hydroxy-benzoyl)-indolizine, 5.7 g (0.04 mol) of potassium carbonate and 100 ml of methyl ethyl ketone was stirred for 30 minutes at room-temperature. To this reaction medium, 20 g (0.1 mol) of 1, 3-dibromopropane were then added and the mixture was refluxed for 12 hours. After cooling, the mineral salts were filtered out and washed on the filter with methyl ethyl ketone. The solvent was evaporated off under vacuum and the residue was triturated with a minimum of isopropanol and partially purified by column chromatography. In this manner, 2-phenyl-3-[4-(3-bromo-propyl)-oxy-benzoyl]-indolizine was obtained in crude form.

To a solution of 2.6 g (0.006 mol) of 2-phenyl-3-[4-(3-bromo-propyl)-oxy-benzoyl]-indolizine, thus obtained, in 50 ml of toluene, was added, at room temperature, 4 g (0.031 mol) of N,N-di-n-butylamine. The mixture was refluxed for 20 hours and subsequently washed with water. The toluene layer was evaporated to dryness to obtain an oily residue which was purified by elution chromatography (adsorbent : silica). The base so purified was taken up in anhydrous ether to which an ethereal solution of oxalic acid was added. The desired salt precipitated and recrystallized from benzene.

In this manner, 2-phenyl-3-[4-(3-di-n-butylaminopropoxy)-benzoyl]-indolizine acid oxalate was obtained in a yield of 64.4% M.P. 92°–93.5° C.

Following the same procedure as that described above but using the appropriate starting-products, the compounds listed hereunder were prepared:

| Compound | Melting point ° C |
|---|---|
| 2-Phenyl-3-[4-(3-di-n-propylaminopropoxy)-benzoyl]-indolizine acid oxalate | 170–171 (dichlorethane) |
| 2-Phenyl-3-[4-(3-diethylaminopropoxy)-benzoyl]-indolizine acid oxalate | 183 (isopropanol) |
| 2-Phenyl-3-[4-(3-dimethylaminopropoxy)-benzoyl]-indolizine acid oxalate | 189 (isopropanol) |
| 2-(4-Fluoro-phenyl)-3-[4-(3-di-n-butylaminopropoxy)-benzoyl]-indolizine acid oxalate | 120 (isopropanol) |
| 2-(4-Fluoro-phenyl)-3-[4-(3-di-n-propylaminopropoxy)-benzoyl]-indolizine acid oxalate | 145 (isopropanol) |
| 2-(4-Fluoro-phenyl)-3-[4-(3-diethylaminopropoxy)-benzoyl]-indolizine acid oxalate | 151 (methanol) |
| 2-(4-Fluoro-phenyl)-3-[4-(3-dimethylaminopropoxy)-benzoyl]-indolizine acid oxalate | 175 (methanol) |
| 2-(4-Chloro-phenyl)-3-[4-(3-di-n-butylaminopropoxy)-benzoyl]-indolizine acid oxalate | 144–145 (isopropanol) |
| 2-(4-Chloro-phenyl)-3-[4-(3-di-n-propylaminopropoxy)-benzoyl]-indolizine acid oxalate | 129–130 (isopropanol) |
| 2-(4-Chloro-phenyl)-3-[4-(3-diethylaminopropoxy)-benzoyl]-indolizine acid oxalate | 165–166 (methanol) |
| 2-(4-Chloro-phenyl)-3-[4-(3-dimethylaminopropoxy)-benzoyl]-indolizine acid oxalate | 186 (isopropanol) |
| 2-(4-Bromo-phenyl)-3-[4-(3-di-n-butylaminopropoxy)-benzoyl]-indolizine acid oxalate | 139 (isopropanol) |
| 2-(4-Bromo-phenyl)-3-[4-(3-di-n-propylaminopropoxy)-benzoyl]-indolizine acid oxalate | 133 (isopropanol) |
| 2-(4-Bromo-phenyl)-3-[4-(3-diethylaminopropoxy)-benzoyl]-indolizine acid oxalate | 159 (methanol) |
| 2-(4-Bromo-phenyl)-3-[4-(3-dimethylaminopropoxy)-benzoyl]-indolizine acid oxalate | 204 (methanol) |
| 2-(4-Methoxy-phenyl)-3-[4-(3-di-n-butylaminopropoxy)-benzoyl]-indolizine acid oxalate | 143 (isopropanol) |
| 2-(4-Methoxy-phenyl)-3-[4-(3-di-n-propylaminopropoxy)-benzoyl]-indolizine acid oxalate | 121–123 (isopropanol) |
| 2-(4-Methoxy-phenyl)-3-[4-(3-diethylaminopropoxy)-benzoyl]-indolizine acid oxalate | 158 (methanol) |
| 2-(4-Methoxy-phenyl)-3-[4-(3-dimethylaminopropoxy)-benzoyl]-indolizine acid oxalate | 138 (methanol) |
| 2-(2-Bromo-phenyl)-3-[4-(3-di-n-butylaminopropoxy)-benzoyl]-indolizine acid oxalate | 100 |
| 2-(2-Bromo-phenyl)-3-[4-(3-di-n-propylaminopropoxy)-benzoyl]-indolizine acid oxalate | 157 (isopropanol) |
| 2-(2-Bromo-phenyl)-3-[4-(3-diethylaminopropoxy)-benzoyl]-indolizine acid oxalate | 149 (methanol) |
| 2-(2-Bromo-phenyl)-3-[4-(3-dimethylaminopropoxy)-benzoyl]-indolizine acid oxalate | 142 (methanol) |
| 2-(3,4-Dichloro-phenyl)-3-[4-(3-di-n-butylaminopropoxy)-benzoyl]-indolizine acid oxalate | 145–146 (isopropanol) |
| 2-(3,4-Dichloro-phenyl)-3-[4-(3-di-n-propylaminopropoxy)-benzoyl]-indolizine acid oxalate | 144–145 isopropanol |
| 2-(3,4-Dichloro-phenyl)-3-[4-(3-diethylaminopropoxy)-benzoyl]-indolizine acid oxalate | 187–188 (isopropanol) |
| 2-(3,4-Dichloro-phenyl)-3-[4-(3-dimethylaminopropoxy)-benzoyl]-indolizine acid oxalate | 163–165 (isopropanol) |
| 2-(3-Bromo-phenyl)-3-[4-(3-di-n-butylaminopropoxy)-benzoyl]-indolizine acid oxalate | 134 (isopropanol) |
| 2-(3-Bromo-phenyl)-3-[4-(3-di-n-propyl-aminopropoxy)-benzoyl]-indolizine acid oxalate | 135–136 (isopropanol) |
| 2-(3-Bromo-phenyl)-3-[4-(3-dimethyl-aminopropoxy)-benzoyl]-indolizine acid oxalate | 167–168 (isopropanol/methanol) |
| 2-(3-Bromo-phenyl)-3-[4-(3-diethyl-aminopropoxy)-benzoyl]-indolizine acid oxalate | 182 (isopropanol) |
| 2-(3-Chloro-4-methyl-phenyl)-3-[4-(3-di-n-butylaminopropoxy)-benzoyl]-indolizine acid oxalate | 91 (isopropanol) |
| 2-(3-Chloro-4-methyl-phenyl)-3-[4-(3-di-n-propylaminopropoxy)-benzoyl]-indolizine acid oxalate | 150–151 (isopropanol) |
| 2-(3-Chloro-4-methyl-phenyl)-3-[4-(3-diethylaminopropoxy)-benzoyl]-indolizine acid oxalate | |
| 2-(3-Chloro-4-methyl-phenyl)-3-[4-(3-dimethylaminopropoxy)-benzoyl]-indolizine acid oxalate | |

-continued

| Compound | Melting point °C |
|---|---|
| 2-(4-Methyl-phenyl)-3-[4-(3-di-n-butylaminopropoxy)-benzoyl]-indolizine acid oxalate | 148–149 (isopropanol) |
| 2-(4-Methyl-phenyl)-3-[4-(3-di-n-propylaminopropoxy)-benzoyl]-indolizine acid oxalate | 141–142 (isopropanol) |
| 2-(4-Methyl-phenyl)-3-[4-(3-diethylaminopropoxy)-benzoyl]-indolizine acid oxalate | 140–142 (isopropanol) |
| 2-(4-Methyl-phenyl)-3-[4-(3-dimethylaminopropoxy)-benzoyl]-indolizine acid oxalate | 162–165 (isopropanol)/methanol) |

EXAMPLE 6

2-(4-Chloro-phenyl)-3-[4-(3-di-n-butylaminopropoxybenzoyl]-indolizine acid oxalate In a flask, a suspension of 4.1 g (0.012 mol) of 2-(4-chloro-phenyl)-3-(4-hydroxy-benzoyl)-indolizine and 3.3 g (0.024 mol) of potassium carbonate in 30 ml of methyl ethyl ketone was stirred for 30 minutes. After this operation, 3.9 g (0.018 mol) of 1-chloro-3-di-n-butylaminopropane were added to the reaction medium which was then refluxed for 12 hours. After cooling, the organic salts were filtered out and washed with acetone. The solvent was evaporated off and the residue was purified by elution chromatography. The base so purified was taken up in anhydrous ether to which an ethereal solution of oxalic acid was added. The precipitate which formed was recrystallized from isopropanol.

In this manner, 2-(4-chloro-phenyl)-3-[4-(3-di-n-butylaminopropoxybenzoyl]-indolizine acid oxalate was obtained in a yield of 50.6%. M.P. 144°–145° C.

EXAMPLE 7

In accordance with known pharmaceutical techniques a soft-gelatin capsule, containing the following ingredients, was prepared:

| Ingredient | mg |
|---|---|
| 2-Ethyl-3-[4-(3-di-n-butylaminopropoxy)-benzoyl]-indolizine hydrochloride | 100 |
| Starches | 99.5 |
| Colloidal silica | 0.5 |
| | 200.0 |

EXAMPLE 8

In accordance with known pharmaceutical techniques, an injectable solution, containing the following ingredients, was prepared:

| Ingredient | mg |
|---|---|
| 2-Ethyl-3-[4-(3-di-n-butylaminopropoxy)-benzoyl]-indolizine hydrochloride | 150 |
| Polysorbate 80 | 150 |
| Benzyl alcohol | 75 |
| Water to 3 ml. | |

EXAMPLE 9

In accordance with known pharmaceutical techniques, a suppository, containing the following ingredients, was prepared:

| Ingredient | mg |
|---|---|
| 2-Ethyl-3-[4-(3-di-n-butylaminopropoxy)-benzoyl]-indolizine hydrochloride | 100 |

-continued

| Ingredient | mg |
|---|---|
| Mixture of mono- and di-glycerides of saturated acids ($C_{12}$ to $C_{18}$) | 1400 |
| | 1500 |

We claim:

1. An indolizine derivative corresponding to the formula:

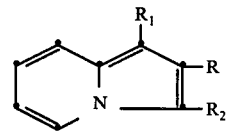

or a pharmaceutically acceptable acid addition salt thereof, wherein R represents a branched- or straight-chain alkyl radical having from 1 to 5 carbon atoms, phenyl, a mono-fluoro-, mono-chloro- or mono-bromo-phenyl, a di-fluoro-, di-chloro- or di-bromo-phenyl radical, a methoxy-phenyl radical or a methyl-phenyl radical optionally substituted on the aromatic moiety by an atom of fluorine, chlorine or bromine and $R_1$ and $R_2$, which are different, represent a hydrogen atom or a group of the formula:

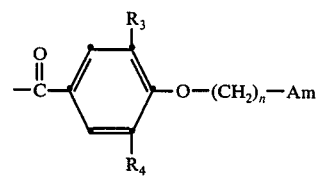

wherein $R_3$ and $R_4$, which are identical, each represent a hydrogen atom or a methyl radical, Am represents dimethylamino, diethylamino, di-n-propylamino di-n-butylamino, and $n$ is an integer in the range of from 2 to 6 inclusive.

2. 2-Ethyl-3-[4-(3-di-n-butylaminopropoxy]-benzoyl-indolizine and pharmaceutically acceptable acid addition salts thereof.

3. 2-Ethyl-3-[4-(3-di-n-butylaminopropoxy)-benzoyl]-indolizine hydrochloride.

4. 2-n-Pentyl-3-[4-(3-di-n-butylaminopropoxy)-benzoyl]-indolizine and pharmaceutically acceptable acid addition salts thereof.

5. 2-n-Butyl-3-[4-(3-di-n-butylaminopropoxy)-benzoyl]-indolizine and pharmaceutically acceptable acid addition salts thereof.

6. 2-Ethyl-3-[4-(4-di-n-butylaminobutoxy)-benzoyl]-indolizine and pharmaceutically acceptable acid addition salts thereof.

7. 2-(2-Bromo-phenyl)-3-[4-(3-diethylaminopropoxy)-benzoyl]-indolizine and pharmaceutically acceptable acid addition salts thereof.

8. 2-(3,4-Dichloro-phenyl)-3-[4-(3-di-n-butylaminopropoxy)-benzoyl]-indolizine and pharmaceutically acceptable acid addition salts thereof.

9. A pharmaceutical composition containing as active ingredient an effective amount of an indolizine derivative of the formula:

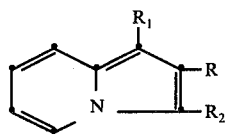

or a pharmaceutically acceptable acid addition salt thereof, wherein R represents a branched- or straight-chain alkyl radical having from 1 to 5 carbon atoms, a phenyl radical, a mono-fluoro-, mono-chloro- or mono-bromo-phenyl, a di-fluoro-, di-chloro- or di-bromo-phenyl radical, a methoxy-phenyl radical or a methyl-phenyl radical optionally substituted on the aromatic moiety by an atom of fluorine, chlorine or bromine and $R_1$ and $R_2$, which are different, represent a hydrogen atom or a group of the formula:

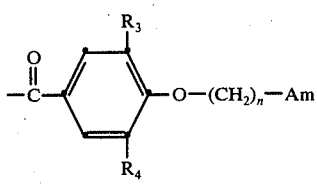

wherein $R_3$ and $R_4$, which are identical, each represent a hydrogen atom or a methyl radical, Am represents dimethylamino, diethylamino, di-n-propylamino or di-n-butylamino, and n is an integer in the range of from 2 to 6 inclusive, in association with a pharmaceutical carrier or excipient therefor.

10. A pharmaceutical composition containing as active ingredient 2-ethyl-3-[4-(3-di-n-butylaminopropoxy)-benzoyl]-indolizine or a pharmaceutically acceptable acid addition salt thereof, in association with a pharmaceutical carrier or excipient therefor.

11. A pharmaceutical composition containing as active ingredient 2-ethyl-3-[4-(3-di-n-butylaminopropoxy)-benzoyl]-indolizine hydrochloride, in association with a pharmaceutical carrier or excipient therefor.

12. A method for treating tachycardia in a subject in need of such treatment which method comprises administering to said subject an effective dose of an indolizine derivative according to claim 1.

13. A method of treating angina pectoris in a subject in need of such treatment which method comprises administering to said subject an effective dose of an indolizine derivative selected from the group consisting of:
2-ethyl-3-[4-(3-di-n-butylaminopropoxy)-benzoyl]-indolizine,
2-n-pentyl-3-[4-(3-di-n-butylaminopropoxy)-benzoyl]-indolizine,
2-n-butyl-3-[4-(3-di-n-butylaminopropoxy)-benzoyl]-indolizine,
2-ethyl-3-[4-(4-di-n-butylaminobutoxy)-benzoyl]-indolizine,
2-(2-bromophenyl)-3-[4-(3-diethylaminopropoxy)-benzoyl]-indolizine,
and 2-(3,4-dichlorophenyl)-3-[4-(3-di-n-butylaminopropoxy)-benzoyl]-indolizine, and pharmaceutically acceptable acid addition salts thereof.

14. A method of treating angina pectoris in a subject in need of such treatment which method comprises administering to said subject an effective dose of 2-ethyl-3-[4-(3-di-n-butylaminopropoxy)-benzoyl]-indolizine or of a pharmaceutically acceptable acid addition salt thereof.

15. A method according to claim 14 wherein the effective dose is 100 mg to 300 mg by oral route or 2 to 3 mg by parenteral route per day to a subject weighing 60 kgs.

16. A method of treating cardiac arrhythmia in a subject in need of such treatment which method comprises administering to said subject an effective dose of 2-ethyl-3-[4-(3-di-n-butylaminopropoxy)-benzoyl]-indolizine or of a pharmaceutically acceptable acid addition salt thereof.

* * * * *